(12) United States Patent
Goto et al.

(10) Patent No.: US 9,160,299 B2
(45) Date of Patent: Oct. 13, 2015

(54) ACOUSTIC WAVE ELEMENT AND ACOUSTIC WAVE ELEMENT SENSOR

(75) Inventors: Rei Goto, Osaka (JP); Hidekazu Nakanishi, Osaka (JP); Hiroyuki Nakamura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 656 days.

(21) Appl. No.: 13/391,416

(22) PCT Filed: Aug. 30, 2010

(86) PCT No.: PCT/JP2010/005318
§ 371 (c)(1),
(2), (4) Date: Feb. 21, 2012

(87) PCT Pub. No.: WO2011/030519
PCT Pub. Date: Mar. 17, 2011

(65) Prior Publication Data
US 2012/0146457 A1 Jun. 14, 2012

(30) Foreign Application Priority Data
Sep. 11, 2009 (JP) .................. 2009-210067

(51) Int. Cl.
*H03H 9/25* (2006.01)
*H03H 9/02* (2006.01)
*G01N 29/02* (2006.01)

(52) U.S. Cl.
CPC ........... *H03H 9/0222* (2013.01); *G01N 29/022* (2013.01); *H03H 9/02818* (2013.01); *H03H 9/02984* (2013.01); *G01N 2291/0423* (2013.01)

(58) Field of Classification Search
USPC ............... 310/313 R, 313 B, 313 C, 338, 340
See application file for complete search history.

(56) References Cited

U.S. PATENT DOCUMENTS 3,699,482 A * 10/1972 Ash et al. ...................... 333/150
3,952,268 A * 4/1976 Schulz et al. ................. 333/155
(Continued)

FOREIGN PATENT DOCUMENTS

| CN | 1745516 | 3/2006 |
| CN | 101399528 | 4/2009 |

(Continued)

OTHER PUBLICATIONS

International Search Report issued Nov. 9, 2010 in International (PCT) Application No. PCT/JP2010/005318.
(Continued)

*Primary Examiner* — Thomas Dougherty
(74) *Attorney, Agent, or Firm* — Wenderoth, Lind & Ponack, L.L.P.

(57) ABSTRACT

An acoustic wave element includes a piezoelectric body, an input IDT electrode, an output IDT electrode, a propagation path provided between the input IDT electrode and the output IDT electrode, a first dielectric layer provided on the piezoelectric body so as to cover the input IDT electrode and the output IDT electrode, and a reactive portion provided on the propagation path and configured to react to a substance to be detected or a binding substance configured to bind with the substance to be detected. The main acoustic wave becomes, in the input IDT electrode and the output IDT electrode, a boundary acoustic wave that propagates between the piezoelectric body and the first dielectric layer, and becomes, in the propagation path, a surface acoustic wave that propagates on an upper surface of the propagation path.

14 Claims, 5 Drawing Sheets

(56) References Cited

U.S. PATENT DOCUMENTS

| | | | |
|---|---|---|---|
| 3,965,444 A * | 6/1976 | Willingham et al. | 333/155 |
| 4,567,393 A | 1/1986 | Asai et al. | |
| 6,476,691 B1 | 11/2002 | Tsuzuki et al. | |
| 7,471,027 B2 | 12/2008 | Kando | |
| 7,608,978 B2 * | 10/2009 | Edmonson et al. | 310/313 R |
| 7,656,070 B2 * | 2/2010 | Kadota et al. | 310/313 R |
| 8,084,916 B2 * | 12/2011 | Goto et al. | 310/313 R |
| 8,436,509 B1 * | 5/2013 | Branch | 310/313 R |
| 2005/0285699 A1 | 12/2005 | Yokota et al. | |
| 2007/0284965 A1 * | 12/2007 | Kadota et al. | 310/313 R |
| 2008/0196478 A1 | 8/2008 | Raghurama et al. | |
| 2009/0085692 A1 | 4/2009 | Tsuda | |
| 2009/0236935 A1 | 9/2009 | Kando | |
| 2009/0272193 A1 * | 11/2009 | Okaguchi et al. | 73/657 |
| 2010/0141088 A1 | 6/2010 | Matsuda et al. | |

FOREIGN PATENT DOCUMENTS

| | | | |
|---|---|---|---|
| EP | 0 542 469 | 5/1993 | |
| EP | 0 920 129 | 6/1999 | |
| JP | 54-051390 | * 4/1979 | H01L 45/00 |
| JP | 57-013802 | * 1/1982 | H03H 5/30 |
| JP | 2001-053581 | 2/2001 | |
| JP | 2007-010378 | 1/2007 | |
| WO | 2008/078481 | 7/2008 | |
| WO | 2008/102577 | 8/2008 | |
| WO | 2009/022410 | 2/2009 | |

OTHER PUBLICATIONS

Chinese Search Report issued Dec. 4, 2013 in corresponding application No. 201080037249.X (in English).

European Search Report issued Nov. 25, 2013 in corresponding Application No. 10 81 5120.

* cited by examiner

Distance (λ) from boundary surface

FIG. 10 – PRIOR ART

ACOUSTIC WAVE ELEMENT AND ACOUSTIC WAVE ELEMENT SENSOR

This application is a U.S. national phase application of PCT international application PCT/JP2010/005318, filed Aug. 30, 2010.

TECHNICAL FIELD

The present invention relates to an acoustic wave element and an acoustic wave element sensor.

BACKGROUND ART

A conventional acoustic wave element will be described with reference to FIG. 10. FIG. 10 is a sectional view of a conventional acoustic wave element. Acoustic wave element 1 includes piezoelectric body 2, IDT electrode 3 provided on piezoelectric body 2 and exciting a main acoustic wave having a wavelength of λ, dielectric layer 4 provided on piezoelectric body 2 so as to cover IDT electrode 3, contact layer 5 provided on dielectric layer 4, and reactive portion 6 provided on contact layer 5 and reacting to a substance to be detected or a binding substance that binds with the substance to be detected.

In such conventional acoustic wave element 1, the main acoustic wave that is excited by IDT electrode 3 is a surface acoustic wave propagating on a surface of dielectric layer 4. However, since dielectric layer 4 is so thin that energy is distributed over a surface of dielectric layer 4, a problem is caused in which IDT electrode 3 is damaged by an external factor, and performance thereof deteriorates during use or during a manufacturing process of acoustic wave element 1.

For example, Patent Literature 1 is known as conventional art literature information related to the invention of this application.

CITATION LIST

Patent Literature

PTL 1: International Publication WO 2008/102577

SUMMARY OF THE INVENTION

An acoustic wave element according to the present invention includes a piezoelectric body, an input IDT electrode provided on the piezoelectric body and exciting a main acoustic wave, an output IDT electrode provided on the piezoelectric body and outputting a signal by receiving the main acoustic wave, a propagation path provided between the input IDT electrode and the output IDT electrode, and a first dielectric layer provided on the piezoelectric body so as to cover the input IDT electrode and the output IDT electrode. The main acoustic wave becomes, in the input IDT electrode and the output IDT electrode, a boundary acoustic wave that propagates between the piezoelectric body and the first dielectric layer, and becomes, in the propagation path, a surface acoustic wave that propagates on an upper surface of the propagation path.

With this structure, it is possible to prevent the input IDT electrode and the output IDT electrode from being damaged by an external factor and deteriorating in performance during use of the acoustic wave element as a sensor or during a manufacturing process thereof.

BRIEF DESCRIPTION OF DRAWINGS

FIG. 10 is a sectional view of a conventional acoustic wave element.

DESCRIPTION OF EMBODIMENTS

First Exemplary Embodiment

Figure 1:
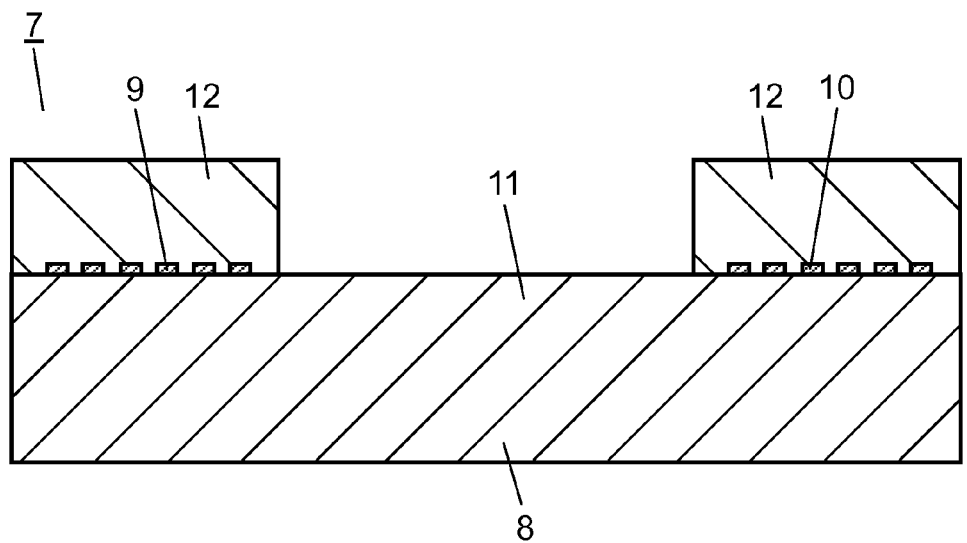
FIG. 1 is a sectional view of an acoustic wave element according to a first exemplary embodiment of the present invention.

Hereinafter, an acoustic wave element according to a first exemplary embodiment of the present invention will be described with reference to the drawings. FIG. 1 is a sectional view of the acoustic wave element according to the first exemplary embodiment.

Referring to FIG. 1, acoustic wave element 7 is a transversal type acoustic wave element including piezoelectric body 8, input IDT (InterDigital Transducer) electrode 9 provided on piezoelectric body 8 and exciting a main acoustic wave such as, for example, an SH (Shear-Horizontal) wave having a wavelength of λ, output IDT electrode 10 provided on piezoelectric body 8 and outputting a signal by receiving the main acoustic wave, and propagation path 11 provided between input IDT electrode 9 and output IDT electrode 10. Further, acoustic wave element 7 includes first dielectric layer 12 having a film thickness equal to or greater than 0.8 times the wavelength λ and provided on piezoelectric body 8 so as to cover input IDT electrode 9 and output IDT electrode 10.

Although not illustrated in FIG. 1, acoustic wave element 7 may include a reactive portion (not illustrated) provided above the propagation path and reacting to a substance to be detected or a binding substance that binds with the substance to be detected.

Piezoelectric body 8 is formed of a single crystal piezoelectric substrate having a plate thickness of about 100 μM to 350 μM, and for example, is a substrate of lithium niobate, lithium tantalate, quartz, or potassium niobate.

Input IDT electrode 9 and output IDT electrode 10 are interdigital electrodes having a normalized film thickness of about 0.01λ to 0.12λ, and are structured of a single metal such as aluminum, copper, silver, gold, titanium, tungsten, platinum, molybdenum, or chromium, or an alloy including these metals as a main component, or a lamination of these metals. In particular, it is preferable to use gold having resistance to corrosion and a large mass as a material for IDT electrodes 9 and 10.

First dielectric layer 12 is made of, for example, silicon oxide, diamond, silicon, silicon nitride, aluminum nitride, or aluminum oxide. The main acoustic wave can be confined in a boundary portion between first dielectric layer 12 and piezoelectric body 8 by selecting first dielectric layer 12 so that a speed of a slowest bulk wave propagating in first dielectric layer 12 becomes greater than a speed of the main acoustic wave that is excited by input IDT electrode 9 or output IDT electrode 10. The speed of the main acoustic wave in input IDT electrode 9 or output IDT electrode 10 is decided mainly by a material of first dielectric layer 12 and a material and a film thickness of IDT electrodes 9 and 10.

Figure 2:
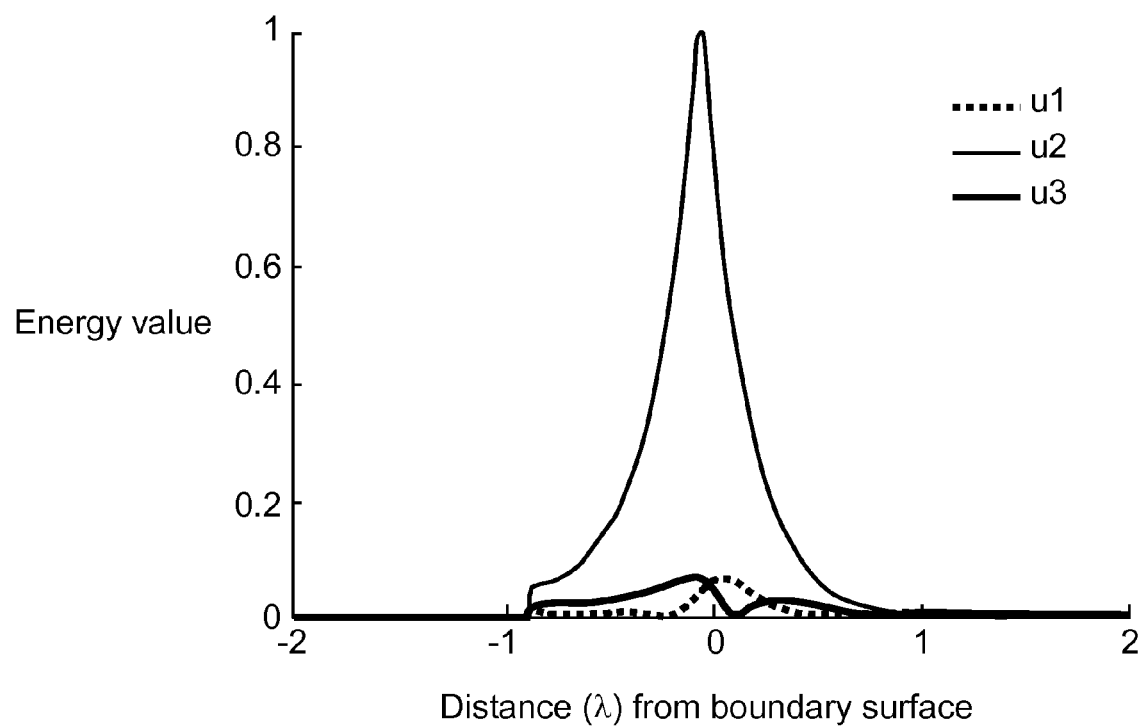
FIG. 2 is an energy distribution chart of the acoustic wave element according to the first exemplary embodiment of the present invention.

Assuming that the wavelength of the main acoustic wave that is excited by input IDT electrode 9 is represented by $\lambda$, it is preferable that a film thickness of first dielectric layer 12 be a film thickness of $0.8\lambda$ or greater. Accordingly, as illustrated in FIG. 2, it is possible to confine the main acoustic wave in IDT electrodes 9 and 10 inside acoustic wave element 7. Here, a vertical axis of FIG. 2 represents an energy value when a maximum energy value of the main acoustic wave is assumed as 1, and a horizontal axis of FIG. 2 represents a distance normalized by the wavelength $\lambda$ of the main acoustic wave when a boundary surface between IDT electrodes 9 and 10 and piezoelectric body 8 is assumed as zero, and a thickness direction (downward direction in FIG. 1) of piezoelectric body 8 is assumed as a positive direction. Reference numerals u1, u2, and u3 in FIG. 2 represent a longitudinal wave component, a transverse wave component, and an in-depth component of the energy of the main acoustic wave, respectively. The same is also applied to FIG. 8 which will be described later.

Preferably, if a film thickness of first dielectric layer 12 is equal to or greater than twice the wavelength $\lambda$ of the SH wave which is the main acoustic wave, the main acoustic wave can be confined almost perfectly in acoustic wave element 7. If a medium such as, for example, silicon oxide having a frequency-temperature characteristic opposite to that of piezoelectric body 8 is used as first dielectric layer 12, it is possible to improve the frequency-temperature characteristic of acoustic wave element 7. It is also possible to achieve a reduction in profile of acoustic wave element 7 by making the film thickness of first dielectric layer 12 equal to or less than $5\lambda$.

In this manner, the main acoustic wave excited by input IDT electrode 9 propagates, in input IDT electrode 9, as a boundary wave in a boundary between first dielectric layer 12 and piezoelectric body 8; propagates, in propagation path 11, as a surface acoustic wave including the main acoustic wave concentrating on a surface of piezoelectric body 8; and, in output IDT electrode 10, becomes a boundary wave again that propagates in the boundary between first dielectric layer 12 and piezoelectric body 8 as illustrated in FIG. 2.

That is, in acoustic wave element 7 according to the first exemplary embodiment of the present invention, by arranging the main acoustic wave as a surface wave in propagation path 11, it is possible to maintain a sensing sensitivity when, for example, the acoustic wave element is used as a sensor. In addition, since input IDT electrode 9 and output IDT electrode 10 are covered by thick first dielectric layer 12, it is possible to prevent input IDT electrode 9 and output IDT electrode 10 from being damaged by an external factor and deteriorating in performance during use or during a manufacturing process of acoustic wave element 7.

Figure 3:
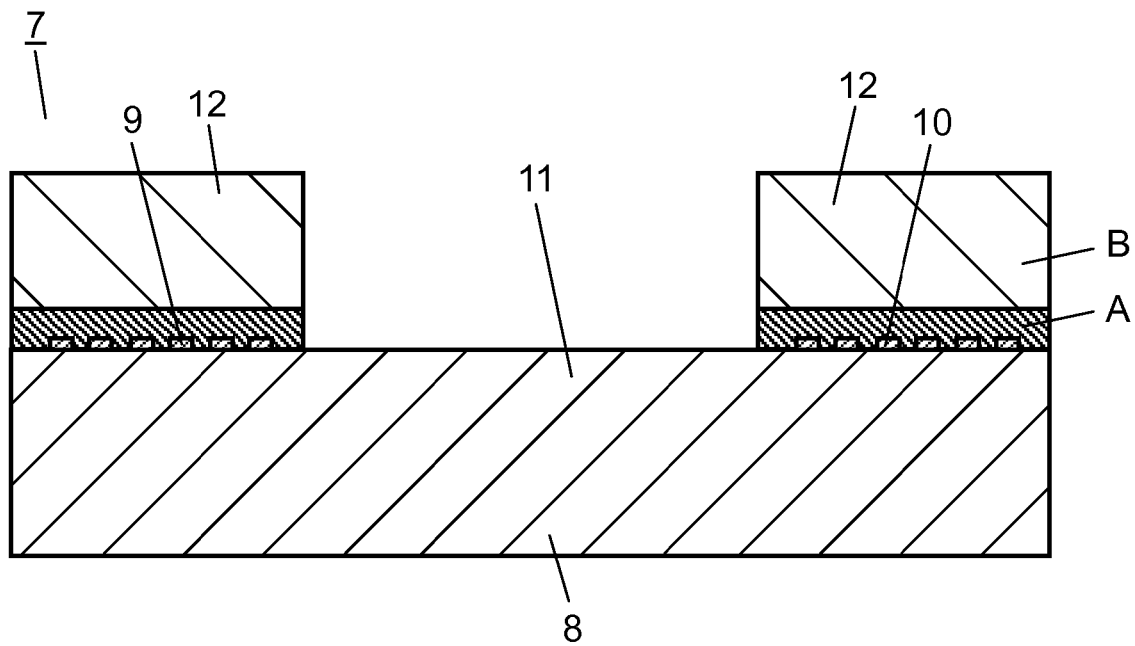
FIG. 3 is another sectional view of the acoustic wave element according to the first exemplary embodiment of the present invention.

Moreover, as illustrated in FIG. 3, first dielectric layer 12 may be structured of a plurality of dielectric layers. In this case, for dielectric layer A as a first layer that covers input IDT electrode 9 and output IDT electrode 10, for example, silicon oxide which is a medium having a frequency-temperature characteristic opposite to that of piezoelectric body 8 is used. For dielectric layer B as a second layer formed on the first layer, for example, diamond, silicon nitride, aluminum nitride, or aluminum oxide, which is a medium in which a speed of a slowest bulk wave propagating in the dielectric layer is greater than that of the main acoustic wave propagating in IDT electrodes 9 and 10, is used. With this arrangement, it is possible to achieve both the desired frequency-temperature characteristic and confinement of the main acoustic wave.

Figure 4:
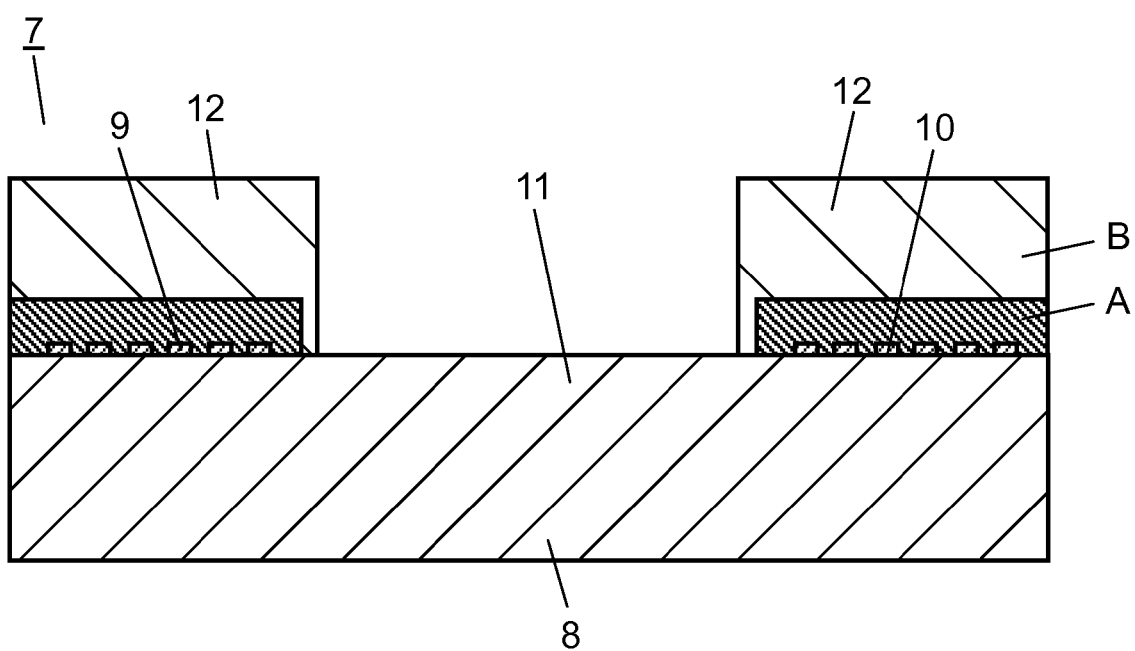
FIG. 4 is another sectional view of the acoustic wave element according to the first exemplary embodiment of the present invention.

Further, as illustrated in FIG. 4, it is preferable to provide a structure in which dielectric layer B which is the second layer and a medium allowing a high propagation speed of the bulk wave covers a side surface of dielectric layer A which is the first layer in a boundary portion between propagation path 11 and input IDT electrode 9 and/or output IDT electrode 10. Accordingly, energy of the main acoustic wave infiltrates from a surface into piezoelectric body 8 in the boundary portion between IDT electrodes 9 and 10 and propagation path 11, and therefore a loss caused by reflection of the main acoustic wave can be prevented.

Figure 5:
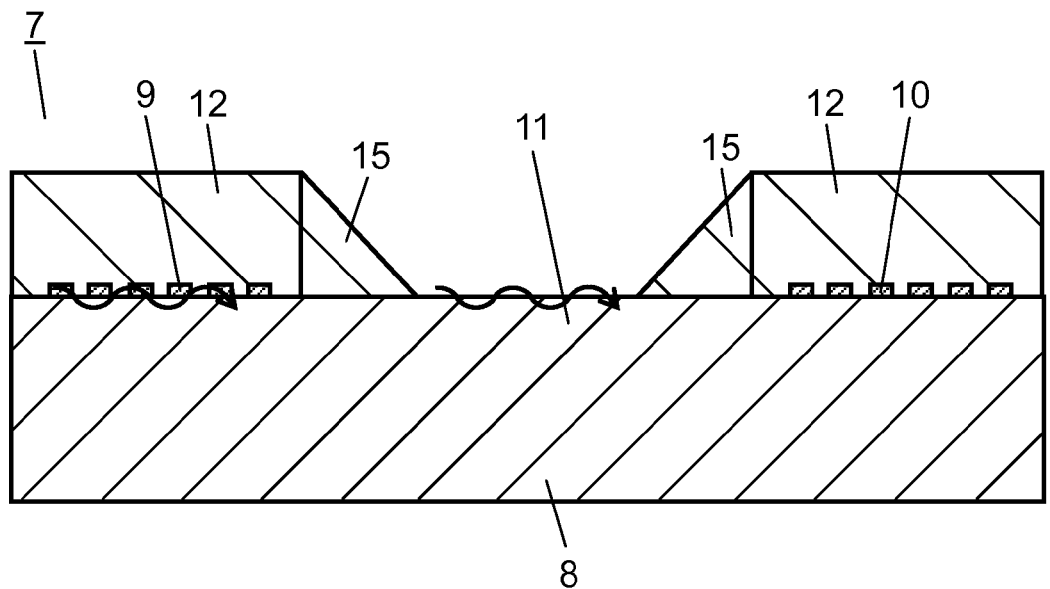
FIG. 5 is another sectional view of the acoustic wave element according to the first exemplary embodiment of the present invention.

As illustrated in FIG. 5, taper portion 15 in which first dielectric layer 12 widens downwardly is provided in a boundary portion between propagation path 11 and input IDT electrode 9 and/or output IDT electrode, so that an acoustic impedance mismatch is alleviated, reflection of the main acoustic wave can be suppressed, and, as a result, acoustic wave element 7 is provided with an excellent electric characteristic.

Figure 6:
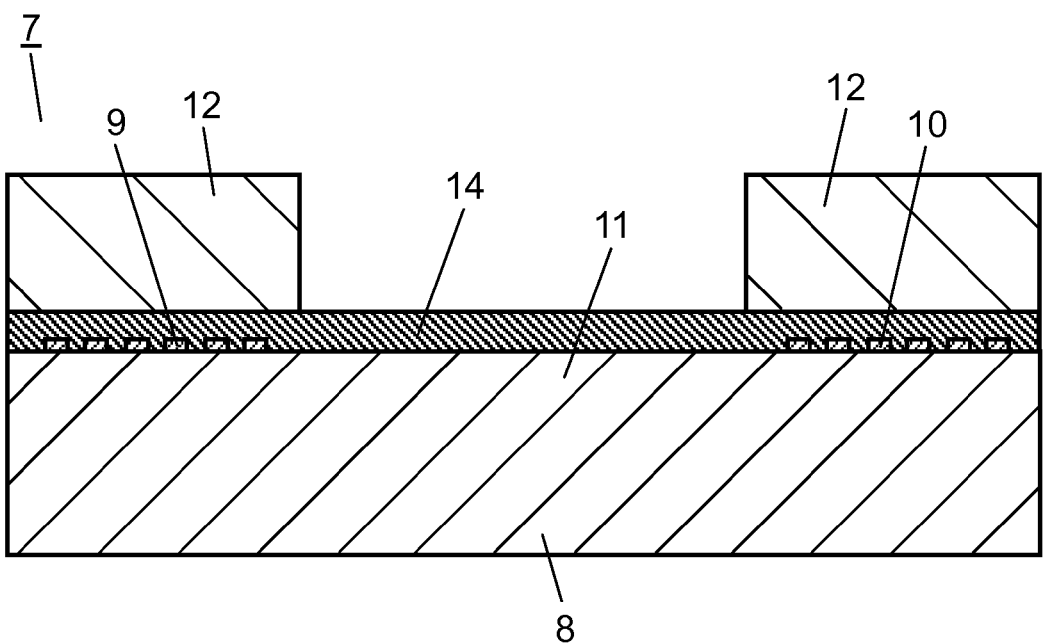
FIG. 6 is another sectional view of the acoustic wave element according to the first exemplary embodiment of the present invention.

Further, as illustrated in FIG. 6, it is also possible to provide second dielectric layer 14 having a film thickness equal to or smaller than 0.4 times of a wavelength $\lambda$ of the main acoustic wave on propagation path 11, and provide a reactive portion (not illustrated) on second dielectric layer 14. In this case as well, by arranging the main acoustic wave as a surface wave in propagation path 11 that performs sensing, it is possible to maintain a sensing sensitivity when, for example, the acoustic wave element is used as a sensor. In addition, since input IDT electrode 9 and output IDT electrode 10 are covered by thick first dielectric layer 12, it is possible to prevent input IDT electrode 9 and output IDT electrode 10 from being damaged by an external factor and deteriorating in performance during use or during a manufacturing process of acoustic wave element 7. The normalized film thickness of second dielectric layer 14 is made equal to or smaller than $0.4\lambda$ because it can suppress an energy loss caused when the main acoustic wave is converted from a boundary wave into a surface wave or from a surface wave to a boundary wave in the boundary portion between IDT electrodes 9 and 10 and propagation path 11. If a medium such as, for example, silicon oxide having a frequency-temperature characteristic opposite to that of piezoelectric body 8 is used for second dielectric layer 14, it is possible to improve the frequency-temperature characteristic of acoustic wave element 7.

Figure 7:
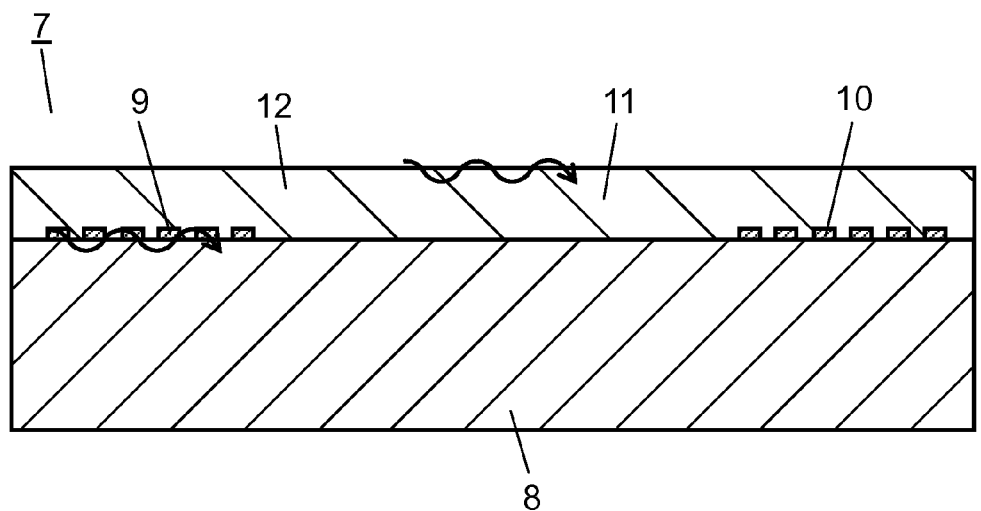
FIG. 7 is another sectional view of the acoustic wave element according to the first exemplary embodiment of the present invention.

Furthermore, as illustrated in FIG. 7, in the case where first dielectric layer 12 having an even thickness is placed on all of input IDT electrode 9, output IDT electrode 10, and propagation path 11, it serves the purpose if the main acoustic wave becomes a boundary acoustic wave in input IDT electrode 9 and output IDT electrode 10 to propagate between piezoelectric body 8 and first dielectric layer 12, and becomes a surface acoustic wave propagating along an upper surface of the propagation path in propagation path 11.

Specifically, a material and a film thickness of first dielectric layer 12 and a material and a film thickness of IDT electrodes 9 and 10 are determined such that a speed of the main acoustic wave excited by a mass addition effect of the electrode becomes smaller than the slowest propagation speed of the bulk wave propagating in first dielectric layer 12 in IDT electrodes 9 and 10, and the speed of the main acoustic wave, without a mass addition effect of IDT electrodes 9 and 10, becomes greater, in propagation path 11, than the slowest propagation speed of the bulk wave propagating in first dielectric layer 12.

Figure 8:
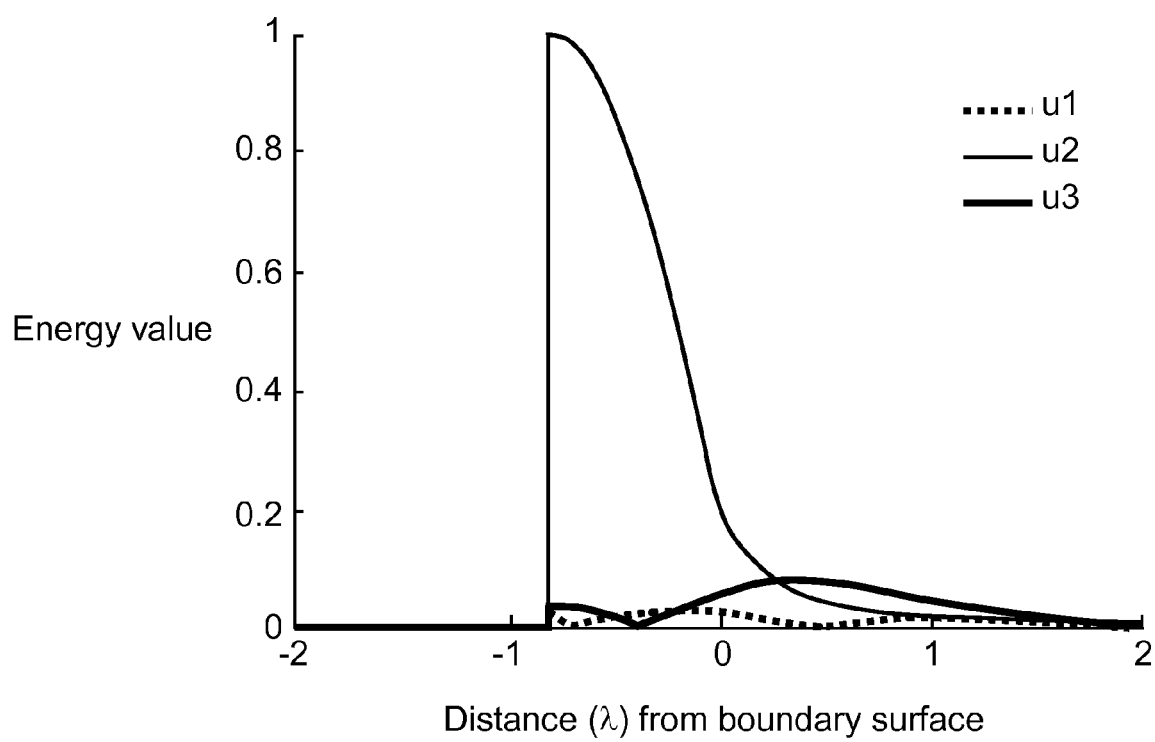
FIG. 8 is another energy distribution chart of the acoustic wave element according to the first exemplary embodiment of the present invention.

FIG. 8 illustrates an energy distribution chart in the case where, for example, 15-degree rotation Y-cut X-propagation lithium niobate is used for piezoelectric body 8, gold having a normalized film thickness of 0.08λ or greater is used for IDT electrodes 9 and 10, and silicon oxide is used for first dielectric layer 12.

As illustrated in FIG. 8, in the case where IDT electrodes 9 and 10 are made of a metal of a material equivalent to gold having a normalized film thickness equal to or greater than 0.08λ, and the normalized film thickness of first dielectric layer 12 made of silicon oxide is equal to or greater than 0.8λ, the main acoustic wave becomes a boundary acoustic wave, in input IDT electrode 9 and output IDT electrode 10, having an energy distribution concentrating in the vicinity of IDT electrode 9, and becomes a surface acoustic wave, in the propagation path, having an energy distribution concentrating on a surface of first dielectric layer 12, because no mass addition effect by the electrode is provided.

That is, in acoustic wave element 7, by converting the main acoustic wave into a surface wave in propagation path 11, it is possible to maintain the sensing sensitivity when the acoustic wave element is applied as, for example, a sensor. In addition, since input IDT electrode 9 and output IDT electrode 10 are covered by thick first dielectric layer 12, it is possible to prevent input IDT electrode 9 and output IDT electrode 10 from being damaged by an external factor and deteriorating in performance during use or during a manufacturing process of acoustic wave element 7.

Second Exemplary Embodiment

Figure 9:
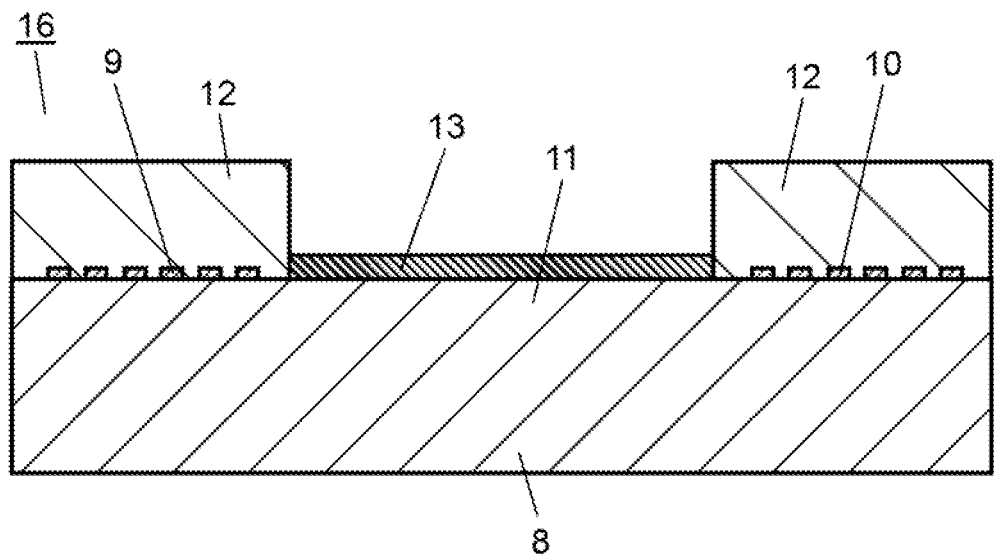
FIG. 9 is a sectional view of an acoustic wave element sensor according to the first exemplary embodiment of the present invention.
Figure 9:
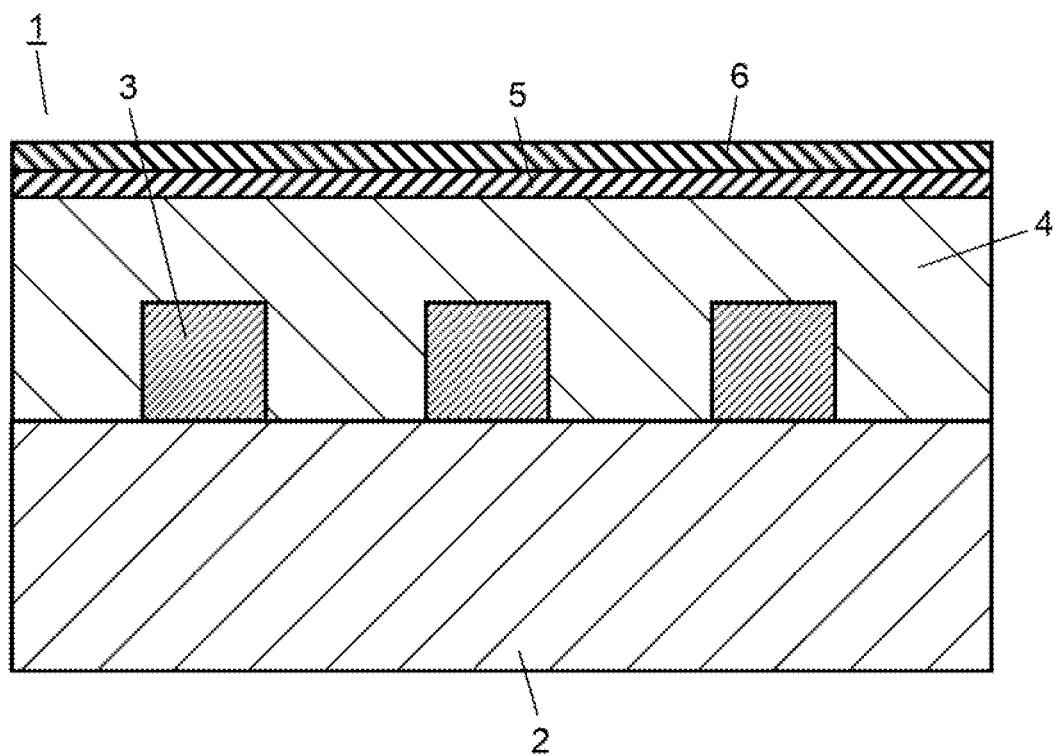

As illustrated in FIG. 9, for example, a case in which reactive portion 13 formed of a specific substance is provided on propagation path 11 will be described in detail. In this case, acoustic wave element 7 according to the present invention can be used as acoustic wave element sensor 16.

Reactive portion 13 can be formed of an arbitrary organic material film such as an artificial cell membrane that reacts to a substance to be detected or a binding substance that binds with the substance to be detected, or a metallic film made of a single metal such as nickel, copper, gold, cobalt, or zinc, or an alloy thereof. Reactive portion 13 may not be in a film shape but may be in a form of reactive particle formed of liposome in a particle shape, for example. Reactive portion 13 also may include an adhesive layer (not illustrated) formed of titanium or the like in an interface between piezoelectric body 8 and reactive portion 13.

Hereinafter, a method for measuring, for example, His-tagged protein in the case where reactive portion 13 is formed of nickel will be described below.

First, a frequency characteristic, when a reference liquid which does not contain the His-tagged protein is made contact, is measured.

Subsequently, a sample in which the His-tagged protein is contained in a liquid is made contact with reactive portion 13, reactive portion 13 is allowed to absorb the His-tagged protein, and the frequency characteristic of acoustic wave element sensor 16 is measured.

Presence or absence of the His-tagged protein in the sample is detected based on a difference between a resonance frequency of the frequency characteristic when the reference liquid obtained in this manner is made contact with reactive portion 13 and a resonance frequency of the frequency characteristic when the sample in which the His-tagged protein is contained in the liquid is made contact with reactive portion 13.

It is also possible to detect a concentration of the His-tagged protein by creating a calibration curve in advance in the following manner. Specifically, the frequency characteristic of acoustic wave element sensor 16 is measured using standard samples including the His-tagged proteins of a plurality of known concentrations. The calibration curve is created based on a difference between resonance frequencies of a plurality of types obtained from the frequency characteristic when the standard samples of the plurality of known concentrations are made contact and the resonance frequency when the reference liquid is made contact. Then, the resonance frequency of acoustic wave element sensor 16 for an unknown sample containing the His-tagged protein is detected, a difference between the detected result and the resonance frequency of acoustic wave element sensor 16 for the reference liquid is obtained, and the concentration of the His-tagged protein is obtained based on the calibration curve.

In acoustic wave element sensor 16 according to the present invention, since input IDT electrode 9 and output IDT electrode 10 are covered by thick dielectric layer 12, it is possible to prevent input IDT electrode 9 and output IDT electrode 10 from being damaged by an external factor and deteriorating in performance during use or during a manufacturing process of acoustic wave element sensor 16.

In the first exemplary embodiment, the SH wave is used as the main acoustic wave. However, in addition to the SH wave, it is also possible to use, as the main acoustic wave, a Raleigh wave having a propagation direction component and a depth direction component as a displacement component which is obtained by changing a cut angle of piezoelectric body 8. Accordingly, confinement of the main acoustic wave propagating on propagation path 11 can be further strengthened, and the sensing sensitivity can be improved.

In the first exemplary embodiment, although propagation path 11 has an open surface, this may be covered with an electrode (not illustrated). By covering with the electrode, the confinement of the main acoustic wave propagating on propagation path 11 into the surface is further strengthened, and the sensing sensitivity is improved by an effect of a short circuit and an effect of mass loading.

Further, in the first exemplary embodiment, a transversal type element of acoustic wave element 7 or acoustic wave element sensor 16 is shown. However, the present invention is not limited thereto, and, for example, acoustic wave element 7 may be a resonator element, a DMS (double mode surface acoustic wave) element, a ladder type acoustic wave element, or the like.

INDUSTRIAL APPLICABILITY

The acoustic wave element according to the present invention has a feature of, for example, suppressing deterioration in sensor characteristic, and can be applied to an electronic device such as medical equipment.

REFERENCE MARKS IN THE DRAWINGS

7 Acoustic wave element
8 Piezoelectric body
9 Input IDT electrode
10 Output IDT electrode
11 Propagation path
12 First dielectric layer
13 Reactive portion
14 Second dielectric layer
15 Taper portion

The invention claimed is:

1. An acoustic wave element comprising:
a piezoelectric body;
an input IDT electrode provided on the piezoelectric body and configured to excite a main acoustic wave;
an output IDT electrode provided on the piezoelectric body and configured to output a signal by being configured to receive the main acoustic wave;
a propagation path provided between the input IDT electrode and the output IDT electrode;
a first dielectric layer provided on the piezoelectric body so as to cover the input IDT electrode and the output IDT electrode; and
a reactive portion provided above the propagation path and configured to react to a substance to be detected or a binding substance configured to bind with the substance to be detected,
wherein the first dielectric layer has a film thickness equal to or greater than 0.8 times a wavelength of a main acoustic wave, and
wherein the main acoustic wave is configured to become, in the input IDT electrode and the output IDT electrode, a boundary acoustic wave that is configured to propagate between the piezoelectric body and the first dielectric layer, and become, in the propagation path, a surface acoustic wave that is configured to propagate on an upper surface of the propagation path.

2. The acoustic wave element according to claim 1, wherein:
the first dielectric layer includes a dielectric layer A formed of silicon oxide and structured so as to cover the input IDT electrode and the output IDT electrode, and a dielectric layer B provided on the dielectric layer A, and
the dielectric layer B is structured to cover a side surface of the dielectric layer A in a boundary portion between the propagation path and the input IDT electrode or the output IDT electrode.

3. The acoustic wave element according to claim 1, wherein
the first dielectric layer includes a taper portion narrowed in a direction from the input IDT electrode or the output IDT electrode to the propagation path.

4. The acoustic wave element according to claim 1, wherein
the first dielectric layer is provided on the input IDT electrode, the output IDT electrode, and the propagation path.

5. The acoustic wave element according to claim 1, wherein the reactive portion is provided directly on the piezoelectric body.

6. The acoustic wave element according to claim 1, further comprising:
a second dielectric layer provided between the reactive portion and the piezoelectric body.

7. The acoustic wave element according to claim 6, wherein
a film thickness of the second dielectric layer is not greater than the film thickness of the first dielectric layer.

8. The acoustic wave element according to claim 7, wherein
the second dielectric layer has a film thickness equal to or smaller than 0.4 times the wavelength of the main acoustic wave.

9. The acoustic wave element according to claim 1, wherein
the film thickness of the first dielectric layer is equal to or greater than 2.0 times the wavelength of the main acoustic wave.

10. The acoustic wave element according to claim 1, wherein
the reactive portion is not disposed above the input IDT electrode and the output IDT electrode.

11. The acoustic wave element according to claim 1, wherein
the input IDT electrode has a first portion which is nearest to the propagation path and a second portion which is farthest from the propagation path in a cross sectional view,
the output IDT electrode has a third portion which is nearest to the propagation path in the cross sectional view, and
a length between the first portion and the third portion is larger than a length between the first portion and the second portion in the cross sectional view.

12. The acoustic wave element according to claim 1, further comprising:
a dielectric material disposed on a boundary portion between the reactive portion and the input IDT electrode.

13. The acoustic wave element according to claim 1, wherein
the first dielectric layer comprises a first portion and a second portion spaced apart from the first portion; the first portion being provided on the piezoelectric body so as to cover the input IDT electrode, and the second portion being provided on the piezoelectric body so as to cover the output IDT electrode.

14. A method for operating an acoustic wave element comprising a piezoelectric body; an input IDT electrode provided on the piezoelectric body; an output IDT electrode provided on the piezoelectric body; a propagation path provided between the input IDT electrode and the output IDT electrode; and a dielectric layer provided on the piezoelectric body so as to cover the input IDT electrode and the output IDT electrode, the method comprising;
exciting a first boundary acoustic wave that propagates between the piezoelectric body and the first dielectric layer in the input IDT electrode;
propagating a surface acoustic wave that is transformed from the first boundary acoustic wave in the propagation path; and
receiving a second boundary acoustic wave that is transformed from the surface acoustic wave and propagates between the piezoelectric body and the first dielectric layer in the output IDT electrode.

* * * * *